(12) United States Patent
Coull et al.

(10) Patent No.: US 7,968,289 B2
(45) Date of Patent: Jun. 28, 2011

(54) TURN OVER PROBES AND USE THEREOF FOR NUCLEIC ACID DETECTION

(75) Inventors: James M. Coull, Westford, MA (US); Lawrence A. Haff, Westborough, MA (US); Joshua A. Bittker, Cambridge, MA (US); Xiaoyu Li, Arlington, MA (US); Larry W. McLaughlin, Dover, MA (US)

(73) Assignee: Ensemble Therapeutics Corporation, Cambridge, MA (US)

( * ) Notice: Subject to any disclaimer, the term of this patent is extended or adjusted under 35 U.S.C. 154(b) by 312 days.

(21) Appl. No.: 11/913,521

(22) PCT Filed: May 3, 2006

(86) PCT No.: PCT/US2006/016999
§ 371 (c)(1),
(2), (4) Date: Feb. 4, 2009

(87) PCT Pub. No.: WO2007/008276
PCT Pub. Date: Jan. 18, 2007

(65) Prior Publication Data
US 2009/0280477 A1    Nov. 12, 2009

Related U.S. Application Data

(60) Provisional application No. 60/677,056, filed on May 3, 2005.

(51) Int. Cl.
*C12Q 1/68*   (2006.01)
*C07H 21/02*  (2006.01)
*C07H 21/04*  (2006.01)
(52) U.S. Cl. .............. 435/6; 536/23.1; 536/24.3
(58) Field of Classification Search ..... 435/6; 536/23.1, 536/24.3
See application file for complete search history.

(56) References Cited

U.S. PATENT DOCUMENTS

| | | | |
|---|---|---|---|
| 5,660,988 A * | 8/1997 | Duck et al. | 435/6 |
| 5,691,142 A * | 11/1997 | Dahlberg et al. | 435/6 |
| 5,980,861 A * | 11/1999 | Hnatowich et al. | 424/1.69 |
| 6,103,476 A | 8/2000 | Tyagi et al. | |
| 6,485,901 B1 | 11/2002 | Gildea et al. | |
| 6,831,166 B2 * | 12/2004 | Manoharan et al. | 536/23.1 |
| 7,070,928 B2 | 7/2006 | Liu et al. | |
| 7,122,364 B1 * | 10/2006 | Lyamichev et al. | 435/199 |
| 7,223,545 B2 | 5/2007 | Liu et al. | |
| 7,442,160 B2 | 10/2008 | Liu et al. | |
| 7,491,494 B2 | 2/2009 | Liu et al. | |
| 7,557,068 B2 | 7/2009 | Liu et al. | |
| 7,771,935 B2 | 8/2010 | Liu et al. | |
| 2002/0127590 A1 | 9/2002 | Erikson et al. | |
| 2003/0119020 A1 * | 6/2003 | Stevens et al. | 435/6 |
| 2003/0235862 A1 * | 12/2003 | Arkin et al. | 435/7.1 |
| 2004/0137494 A1 * | 7/2004 | Narayanan | 435/6 |
| 2005/0233381 A1 | 10/2005 | Liu et al. | |
| 2006/0223086 A1 | 10/2006 | Liu et al. | |
| 2007/0154899 A1 | 7/2007 | Coull et al. | |
| 2008/0318807 A1 | 12/2008 | Liu et al. | |
| 2009/0149347 A1 | 6/2009 | Liu et al. | |
| 2009/0163371 A1 | 6/2009 | Stern et al. | |
| 2009/0203530 A1 | 8/2009 | Liu et al. | |
| 2009/0275142 A1 | 11/2009 | Huang et al. | |
| 2009/0280477 A1 * | 11/2009 | Coull et al. | 435/6 |
| 2010/0152099 A1 | 6/2010 | Lee et al. | |
| 2010/0159446 A1 | 6/2010 | Haff et al. | |
| 2010/0159455 A1 | 6/2010 | Landsman et al. | |

OTHER PUBLICATIONS

Tyagi et al., Molecular Beacons: Probes that fluoresce upon Hybridization. Nature Biotechnology 14 :303-308 (Mar. 1996).*
Mag et al., Synthesis and selective cleavage of an oligodeoxynucleotide containing a bridged internucleotide. 5'-phosphorothioate linkage. Nucleic Acids Research 19 (7) : 1437-1441 (1991).*
Kuimelis et al., Cleavage properties of an oligonuclotide containing a bridged internucleotide 5'-phosphorothioate RNA linkage. Nucleic Acids Research 23 (23) :4753-4760 (1995).*
Metelev et al., New chemically reactive dsDNAs containing single internucleotide monophosphoryldithio links: reactivity of 5'-mercapto-oligodeoxyribonucleotides. Nucleic Acids Research 23 (23) :4753-4760 (1995).*
Giulietti et al., An overview of real-time quantitative PCR: applications to quantify cytokine gene expression. Methods 25 (4) : 386-401 (2001).*
Abe et al.,Destabilizing Universal Linkers for Signal Amplification in Self-Ligating Probes for RNA. JACS 126: 13980-13986 (2004).*
Ferentz et al., Synthesis and characterization of disulfide cross-linked oligonucleotides. JACS 115 : 9006-9014 (1993).*
Dirks et al., Triggered amplification by hybridization chain reaction. PNAS 101(43) : 15275-15278(2004).*
Fong et al.,Rapid Solid-Phase Immunoassay for Detection of Methicillin-Resistant *Staphylococcus aureus* Using Cycling Probe Technology. J. of Clinical Microbiology 38(7) : 2525-2529 (2000).*
Abe, et al. (2004) "Destabilizing Universal Linkers for Signal Amplification in Self-Ligating Probes for RNA," *J. Am. Chem. Soc.*, 126:13980-13986.
Dirks, et al. (2004) "Triggered amplification by hybridization chain reaction," *Proc. Natl. Acad. Sci. USA*, 101:15275-15278.
Ferentz, et al. (1991) "Disulfide Cross-Linked Oligonucleotides," *J. Amer. Chem. Soc.*, V.113:4000-4002. Ferentz, et al. (1993) "Synthesis and Characterization of Disulfide Cross-Linked Oligonucleotides," *J. Am. Chem. Soc.*, V.115:9006-9014.
Fidanza and McLaughlin, (1992) "Use of a Thiol Tether for the Site-Specific Attachment of Reporter Groups to DNA," *J. Am. Chem.*, 57:2340-2346.
Flamm, et al. (2001) "Design of multistable RNA molecules," *RNA*, 7:254-265.
Fong, et al. (2000) "Rapid Solid-Phase Immunoassay for Detection of Methicillin-Resistant *Staphylococcus aureus* Using Cycling Probe Technology," *J. Clin. Microbiol.*, 38:2525-2529.
Giulietti, et al. (2001) "An Overview of Real-Time Quantitative PCR: Applications to Quantify Cytokine Gene Expression," *Methods*, 25:386-401.

(Continued)

*Primary Examiner* — Ethan Whisenant

(74) *Attorney, Agent, or Firm* — Goodwin Procter LLP

(57) ABSTRACT

The invention provides turnover probes for use in a variety of detection assays, for example, nucleic acid detection assays. In addition, the invention provides assays, for example, nucleic acid detection assays, using such turnover probes.

14 Claims, 8 Drawing Sheets

OTHER PUBLICATIONS

Kuimelis and McLaughlin (1995) "Cleavage properties of an oligonucleotide containing a bridged internucleotide 5'-phosphorothioate RNA linkage," *Nucl. Acids Res.*, 23:4753-4760.

Mag, et al. (1991) "Synthesis and selective cleavage of an oligodeoxynucleotide containing a bridged internucleotide 5'-phosphorothioate linkage," *Nucleic Acids Research*, 19:1437-1441.

Metelev, et al. (2001) "New chemically reactive dsDNAs containing single internucleotide monophosphoryldithio links: reactivity of 5'-mercapto-oligodeoxyribonucleotides," *Nucleic Acids Research*, 29:4062-4069.

Richards and Logue, (1962) "Changes in Absorption Spectra in the Ribonuclease-S System," *J. Biol. Chem.*, 237:3693-3695.

Sakurai et al., (2005) "DNA-Templated Functional Group Transformations Enable Sequence-Programmed Synthesis Using Small-Molecule Reagents," *J. Am. Chem. Soc.*, 127:1660-1661.

Tyagi et al., (1996) "Molecular Beacons: Probes that Fluoresce upon Hybridization," *Nature Biotechnology*, 14:303-308.

International Preliminary Report on Patentability for International Application No. PCT/US2006/016999, dated Nov. 6, 2007, 8 pages.

International Search Report for International Application No. PCT/US2006/016999, mailed Feb. 22, 2007, 5 pages.

* cited by examiner

TURN OVER PROBES AND USE THEREOF FOR NUCLEIC ACID DETECTION

RELATED APPLICATIONS

This application is the national stage of International (PCT) Patent Application Serial No. PCT/US2006/016999 filed May 3 2006 and published under PCT Article 21(2) in English, which claims the benefit of and priority to U.S. Provisional Patent Application Ser. No. 60/677,056, filed May 3, 2005, the entire disclosure of each of which is incorporated by reference herein.

FIELD OF THE INVENTION

The present invention relates generally to probes and their use in detection assays and, more particularly, the invention relates to turnover probes and their use in detection assays.

BACKGROUND

Oligonucleotide probes have been used for many years in a variety of different in vivo and in vitro diagnostic assays, and as research tools. In assays, the probes have been employed, for example, as detection agents where an oligonucleotide sequence of interest is linked to a detectable label, for example, an enzyme, fluorophore, radiolabel, or other reporter group. In addition, the oligonucleotide probes can be attached to a support, for example, a particle or solid surface, for the purpose of capturing and/or sorting of nucleic acids. In addition, the oligonucleotide probes can be used as primers or modulators of amplification, ligation, and other enzymatically catalyzed reactions.

Diagnostic assays, for example, diagnostic assays for detecting the presence of a target nucleic acid in a test sample, typically fall into one of two general categories. In one category, the target nucleic acid is amplified either directly or indirectly to produce copies of the target or of a target surrogate, either of which can be detected by any number of methods. Examples of target amplification methods include polymerase chain reaction (PCR), reverse transcriptase-polymerase chain reaction (RT-PCR), transcription mediated amplification (TMA), rolling circle amplification (RCA), and ligase chain reaction (LCR), among others. In the other category, the target nucleic acid is not amplified. Rather, the target is detected directly, typically using one or more hybridization probes. There are many formats for this type of assay, which include, for example, a hybridization probe labeled directly (covalently) or indirectly with a reporter group, or solid-phase such as a bead that may be detected is some fashion.

In general, assays where the target is amplified, for example, by PCR, are considered to be both more specific and more sensitive than direct detection assays. However, direct assays generally are considered to be simpler to perform, and often without the need of sophisticated instrumentation. While simplicity can make direct assays more attractive there is a need to improve their sensitivity. The sensitivity of direct assays can be limited because each complementary target nucleic acid only binds to a single labeled probe. This limitation has been addressed using a variety of approaches including, for example, using multiple probes to "paint" the target, using branched or linker-extended probes containing multiple reporter groups, or constructing large "Christmas trees" of probes containing a plurality of reporters (for example, the Urdea b-DNA assay available from Chiron Corporation).

One approach that can be attractive is to have the target nucleic acid (for example, a DNA or RNA molecule) "turnover" a complementary probe or probes that had bound to the target. In this type of assay, the probe turnover or conversion is linked to a detection system. Attempts at constructing such a system have been reported in the literature.

Abe et al. (J. Am. Chem. Soc. (2004) 126: 13980-13986), for example, describe an approach where probe turnover resulted in a 92-fold amplification of the signal in 24 hours. As discussed by Abe et al., a problem that can be experienced when two adjacent probes are ligated either chemically or enzymatically is that the ligated complex invariably is more stable than the starting complex, resulting in "product inhibition." Essentially, the ligation event makes it even harder to achieve probe turnover. Although Abe et al. attempted to address this problem by selectively destabilizing the ligated product by introducing a several-atom-length flexible linker between the two probes so as to interrupt the two complementary half segments complementary to adjacent positions on the target. It was contemplated that this type of complex would be considerably less favorable entropically than having a direct linkage between the two half probes. However, the 92-fold amplification reported in Abe et al. may not be sufficient to make a significant improvement from the standpoint of applying the system to detection of biologically important targets. It has been contemplated that turnovers of 1,000-fold or greater in 30 minutes may be required for this or another approach to be commercially useful.

Fong et al. (J. Clin. Microbiol. (2000) 38: 2525-2529) describe an assay based on "Cycling Probe Technology" (CBT) which includes a turnover system that is enzymatically modulated. In this assay, a mixed DNA-RNA-DNA probe containing centrally located ribonucleotide linkages hybridizes to a complementary target sequence when the target is present in a sample of interest. The enzyme RNAse H, when added, recognizes the resulting hybrid and cleaves the RNA portion of the duplex. As a result, the probe is cleaved and the resulting cleaved complex dissociates because it is less stable than the starting hybrid. The target sequence then is free to bind another DNA-RNA-DNA probe molecule and the cycle repeats. Labels disposed at the end of the cleaved probe fragments can be captured and/or directly detected.

Dirks et al. (Proc. Natl. Acad. Sci. USA (2004) 101: 15275-15278) describe a "Hybridization Chain Reaction" where two hairpin probes are synthesized in such a way that they are complementary to each other in an overlapping (staggered) fashion. As a result, they hybridize to one another to create a long-duplex DNA. The rate of duplex formation when these hairpins are first mixed is very small because the sequences within the hairpins are trapped in a duplex conformation that renders them unable to bind to each other. Upon addition of a trigger molecule (i.e., a target sequence), hybridization of the trigger molecule to a sticky end of one of the hairpins causes that hairpin to open. The opened hairpin then opens another hairpin, and so on, until all the hairpins are consumed. Thus, prior to trigger addition, the system essentially contains a substantial potential energy that is released by addition of a specific trigger sequence.

It has been recognized that in order for assays to be run outside of a controlled laboratory environment by unskilled personnel, and/or without requiring the use of sophisticated sensitive instrumentation, the assays must be simple but yet sensitive. Typically such assays are developed for point of care diagnostics (genetic and infectious disease testing), detection of bacteria and viruses in the environment, food, water, and other beverages, as well as for biothreat detection.

There is a significant need that assays for such applications require little or no sample preparation. As such, the types of complex assays (e.g., PCR and TMA) typically run in clinical or regulated settings such as hospital and reference laboratories, are almost impossible to transition into more demanding uncontrolled settings.

Notwithstanding the foregoing, there is still a need for specific turnover probes that can provide the requisite sensitivity when used in both in vivo and in vitro diagnostic assays.

SUMMARY OF THE INVENTION

The present invention is based, in part, upon the discovery that it is possible to create turnover probes that can provide the requisite sensitivity in nucleic acid assays where the target sequences have not be amplified prior to the detection steps. The nucleic acid probes described herein are designed such that after a probe-nucleic acid complex has been formed, the probe is altered so that it develops a propensity to create a hairpin structure. Once a hairpin structure forms, the probe becomes disassociated from the complex leaving the target nucleic acid available to bind to another probe. When coupled to a detection system, probe turnover can be used to amplify the signal, which in turn can enhance the sensitivity of the assay.

In one aspect, the invention provides a method of disassociating a nucleic acid probe from a target nucleic acid sequence. The method comprises the steps of: (a) combining a nucleic acid probe with a sample suspected of containing the target nucleic acid sequence under conditions to permit the probe to anneal to the target nucleic acid sequence if the target nucleic acid is present in the sample, wherein the nucleic acid probe comprises a chemical moiety, which if modified or removed, permits the nucleic acid probe or a fragment thereof to form a hairpin structure and disassociate from the complex; and (b) providing a reagent capable of modifying or removing the chemical moiety so that if a complex is present in the sample the nucleic acid probe or the fragment thereof forms a hairpin structure and disassociates from the complex.

The method optionally comprises the additional step of detecting a product produced by step (b) indicative of the existence of the complex. Using this approach, it is possible to determine whether a target nucleic acid is present in the sample of interest.

In another aspect the invention provides a method of detecting the presence of a target nucleic acid sequence in a sample. The method comprises the steps of (a) combining with a sample suspected of containing the target nucleic acid sequence a nucleic acid probe capable of annealing to the target nucleic acid sequence to form a complex, wherein the nucleic acid probe comprises a chemical moiety which if modified or removed permits the nucleic acid probe or a fragment thereof to form a hairpin structure and disassociate from the complex; (b) providing a reagent capable of modifying or removing the chemical moiety so that if a complex is present in the sample the nucleic acid probe or the fragment thereof forms a hairpin structure and disassociates from the complex; and c) detecting a product produced by step (b) indicative of the existence of the complex so as to determine whether the target nucleic acid is present in the sample.

In another aspect, the invention provides a method of amplifying a signal indicative of the presence of a target nucleic acid in a sample. The method comprises the steps of: (a) incubating a sample suspected of containing the target nucleic acid with a first nucleic acid probe under conditions to permit the first nucleic acid probe to anneal to the target nucleic acid if present in the sample, wherein the first nucleic acid probe comprises (i) a signal generating moiety capable of producing a detectable event and (ii) a nucleotide sequence that anneals to the target nucleic acid; (b) providing a non-enzymatic turnover inducing reagent that reacts with the first nucleic acid probe to promote separation of the first nucleic acid probe from the target nucleic acid and create a detectable event; and (c) allowing a second nucleic acid probe to bind to the target nucleic acid after the first nucleic acid probe has been separated from the target nucleic acid and produce another detectable event.

In another aspect, the invention provides a turnover probe useful in detecting the presence of a target nucleic acid in a test sample. The probe comprises the following features (i) a nucleic acid sequence complementary to the target nucleic acid, (ii) a chemical moiety associated with the nucleic acid sequence, which if modified or removed by a chemical reagent permits the probe to form a hairpin structure and to disassociate from the complex, and (iii) a detectable label associated with the nucleic acid sequence. The probe optionally includes a quencher associated with the nucleic acid sequence. When a quencher is employed, little or no signal is created in the presence of the quencher. However, once the chemical moiety has been modified or removed and a hairpin structure has been created, the quencher may no longer be available to quench the detectable label. As a result, hairpin formation can, under certain circumstances, result in the development of a signal, such as a colored signal or a fluorescent signal, that can be used to determine whether a target nucleic acid was present in the sample of interest.

In another aspect, the invention provides a composition that occurs during a typical nucleic acid detection assay when turnover probes of the invention are employed. In particular, the composition comprises a target nucleic acid sequence and a nucleic acid probe capable of annealing to the target nucleic acid sequence to form a complex. The nucleic acid probe comprises a chemical moiety which, if modified or removed, permits the nucleic acid probe to form a hairpin structure and disassociate from the complex.

The foregoing aspects and embodiments of the invention may be more fully understood by reference to the following figures, detailed description and claims.

BRIEF DESCRIPTION OF THE FIGURES

The invention may be further understood from the following figures.

DETAILED DESCRIPTION OF THE INVENTION

Figure 1:
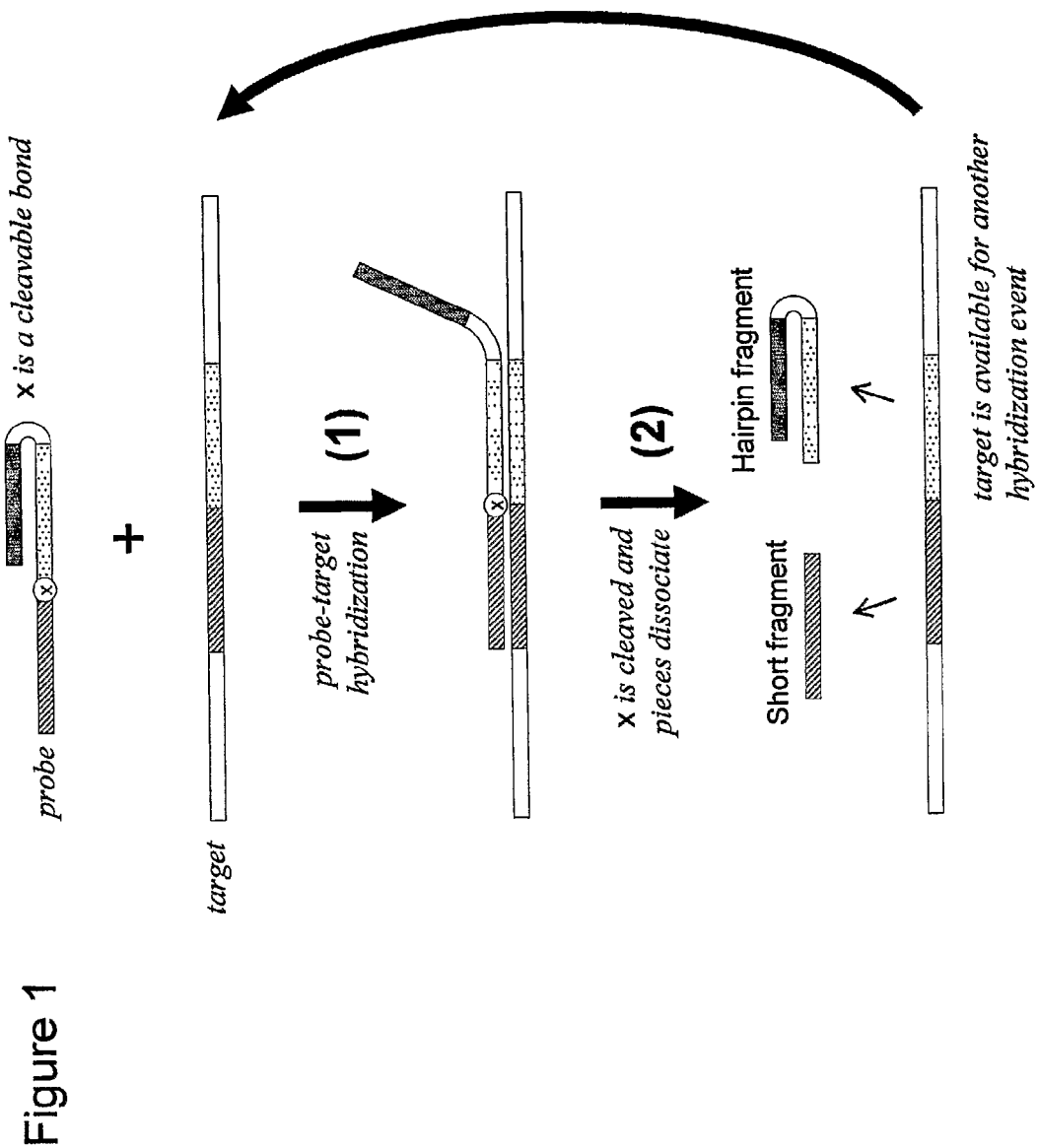
FIG. 1 is a schematic representation of a nucleic acid detection assay where the turnover probe is cleaved to produce a hairpin structure.

The present invention provides turnover probes that facilitate the requisite sensitivity in nucleic acid assays where the target sequences have not been amplified prior to the detection step. The nucleic acid probes described herein are designed such that after a probe-nucleic acid complex has been formed, the probe is altered so that it forms a hairpin structure. Once the hairpin structure has formed, the probe becomes disassociated from the complex leaving the target nucleic acid available to bind to another probe. When coupled to a suitable signal generating moiety, probe turnover can be used to amplify the signal, which in turn can enhance the sensitivity of the assay. By using a properly constructed hairpin and by providing a suitable means to chemically, enzymatically, or catalytically cleave or deblock the hairpin, as a result of its binding to a template (target), it is possible to achieve turnover rates that are meaningful from a diagnostics and research assay standpoint.

The invention permits the skilled artisan to create turnover probes that may be used in nucleic acid detection assays. However, it is contemplated that the probes may be used for other purposes, for example, drug delivery. In essence, the probes, once bound to the target nucleic acid may be released from the target nucleic acid to permit another probe to bind to the same or a similar sequence. As a result, probe turnover can be used to amplify a signal in a nucleic acid detection assay.

The method of disassociating a nucleic acid probe comprises the steps of: (a) combining a nucleic acid probe with a sample suspected of containing the target nucleic acid sequence under conditions to permit the turnover probe to anneal to the target nucleic acid sequence, if the target nucleic acid is present in the sample, wherein the nucleic acid probe comprises a chemical moiety, which if modified or removed, permits the nucleic acid probe or a fragment thereof to form a hairpin structure and disassociate from the complex; and (b) providing a reagent capable of modifying or removing the chemical moiety so that if a complex is present in the sample the nucleic acid probe or the fragment thereof forms a hairpin structure and disassociates from the complex. To the extent that the probe is being used in a nucleic acid detection assay, the method can comprise the additional step of detecting a product produced by step (b) indicative of the existence of the complex. This step can be used to determine whether the target nucleic acid is present in the sample.

In this method, the hairpin structure can comprise a stem and a loop. The reagent provided in step (b) is capable of modifying or removing the chemical moiety so that if a complex is present in the sample, the nucleic acid probe or the fragment thereof forms a hairpin structure and disassociates from the complex. The chemical moiety, when present in or associated with the probe, prevents hairpin formation. The chemical moiety can be selected, for example, from the group consisting of a base, a modified base, an oligonucleotide, a modified oligonucleotide, an internucleotide linkage, a modified internucleotide linkage, a protecting group, a peptide, a protein, a polymer, a bead and a nanoparticle. Modification or removal of the chemical moiety causes the probe to form a hairpin structure and disassociate from the target nucleic acid.

By way of example, the chemical moiety can be a bulky group, for example, an oligonucleotide, chemical side chain, a polymer, a peptide, a protein, a bead or nanoparticle, or the like, that prevents hairpin formation as a result of steric hindrance. The chemical moiety can be covalently or non-covalently associated with the probe. When covalently associated with the probe, this may be, for example, via a chemical bond or linker. Cleavage of the chemical bond or the linker results in the chemical moiety being cleaved from the probe. In the absence of the chemical moiety, the probe, which has a natural propensity to produce a hairpin, forms a hairpin structure. As a result of hairpin formation, the probe becomes disassociated from the target permitting another probe to bind to the same or a similar target sequence.

In another example, the chemical moiety may comprise an internucleotide linkage that connects, for example, a base, modified base, oligonucleotide sequence, or modified oligonucleotide to the turnover probe. The base, modified base, oligonucleotide sequence or modified oligonucleotide sequence anneals to the target sequence when connected to the turnover probe. However, depending upon the choice of the appropriate conditions, once the internucleotide linkage is cleaved, the base, modified base, oligonucleotide, or modified oligonucleotide can disassociate from the target. The loss of these elements permits the turnover probe to form a hairpin structure and disassociate from the target sequence.

In another example, the chemical moiety may comprise a base, modified base, internucleotide linkage, modified oligonucleotide linkage, oligonucleotide sequence, or modified oligonucleotide that is part of the turnover probe. However, depending upon the choice of the appropriate conditions, once the base, modified base, oligonucleotide, modified oligonucleotide, internucleotide linkage, or modified oligonucleotide linkage is modified, the remainder of the turnover probe can then form a hairpin structure and disassociate from the target sequence. Alternatively, once the base, modified base, oligonucleotide, modified oligonucleotide, internucleotide linkage, or modified oligonucleotide linkage is cleaved from the turnover probe, the remainder of the turnover probe can form a hairpin structure and disassociate from the target sequence.

Assuming that the turnover probe is linked to, associated with, or contains a signal generating moiety, it is possible to create a detectable signal when the probe forms a hairpin and becomes disassociated from the target sequence. The sample principles apply irrespective of whether the chemical moiety is modified or removed from the remainder of the turnover probe. Furthermore, the turnover probe can be coupled to a ligand of interest to deliver the ligand to the target sequence.

Following hairpin formation, this probe becomes disassociated from the target and can be replaced with another turnover probe.

The reagent that modifies or removes the chemical moiety (also referred to herein as a turnover inducing reagent) may be a chemical reagent that is provided free in solution. The reagent then acts to modify or cleave the chemical moiety associated with the probe. Alternatively, the reagent that modifies the chemical moiety may be a chemical reagent that that is coupled to or associated with a nucleic acid sequence complementary to the target nucleic acid sequence. Assuming that the reagent is linked to a second nucleic acid sequence capable of annealing to the target nucleic acid sequence, when the second nucleic acid sequence anneals to the target nucleic acid sequence, the reagent modifies or removes the chemical moiety contained in, or associated with, the nucleic acid probe that also is annealed to the target nucleic acid. In this embodiment, the second nucleic acid sequence anneals to a first location of the target nucleic acid sequence and the nucleic acid probe anneals at a second location of the target nucleic acid sequence. The first and second locations can be adjacent one another.

Useful reagents may include an agent selected from the group consisting of a metal, a reducing agent, a chelating agent, a nucleophile, a nucleophilic compound, an electrophile, an electrophilic compound, a catalytic peptide, a catalytic small molecule such as imidazole, a protease, a nuclease, or other protein capable of effecting a chemical transformation.

In addition, the invention provides a method of amplifying a signal indicative of the presence of a target nucleic acid in a sample. The method comprises the steps of: (a) incubating a sample suspected of containing the target nucleic acid with a first nucleic acid probe under conditions to permit the first nucleic acid probe to anneal to the target nucleic acid if present in the sample, wherein the first nucleic acid probe comprises (i) a signal generating moiety capable of producing a detectable event and (ii) a nucleotide sequence that anneals to the target nucleic acid; (b) providing a non-enzymatic turnover inducing reagent that reacts with the first nucleic acid probe to promote separation of the first nucleic acid probe from the target nucleic acid and create a detectable event; and (c) allowing a second nucleic acid probe to bind to the target nucleic acid after the first nucleic acid probe has been separated from the target nucleic acid and produce another detectable event.

In this approach, the signal generating moiety can be covalently attached to the first nucleic acid probe. The signal generating moiety can be a catalyst for another reaction that results in a detectable signal. For example, the signal generating moiety can be a light emitting moiety, where the detectable event is an optical event. Alternatively, the signal generating moiety can comprise one or more chemical moieties, which create a detectable signal on its or their own. Furthermore, the turnover inducing reagent can be attached to a different nucleotide sequence that anneals to the target nucleic acid at a location adjacent to where the probe anneals to the target nucleic acid.

The turnover inducing reagent reacts with the first nucleic acid probe to cause the first nucleic acid probe or a fragment thereof to produce a hairpin structure. Once the first nucleic acid probe or a fragment thereof produces a hairpin structure, the first nucleic acid probe or the fragment thereof becomes disassociated from the target to permit a second nucleic acid probe to bind to the target nucleic acid to produce another detectable event.

Exemplary turnover probes comprise (i) a nucleic acid sequence complementary to the target nucleic acid, (ii) a chemical moiety associated with the nucleic acid sequence, which, if modified or removed by a chemical reagent, permits the probe to form a hairpin structure and to disassociate from the complex, (iii) a signal generating moiety associated with the nucleic acid sequence, and, optionally, (iv) a quencher associated with the nucleic acid sequence.

In one embodiment, the chemical moiety can be disposed within the nucleic acid sequence. Accordingly, the chemical moiety can be a chemical bond or can be defined by at least one atom. In another embodiment, the chemical moiety is attached to the nucleic acid sequence, for example, via a covalent bond. In these embodiments, the chemical moiety can be selected from the group consisting of a base, a modified base, an oligonucleotide, a modified oligonucleotide, a modified internucleotide linkage, a protecting group, a peptide, and a cleavable linker.

During the practice of the methods described herein, the methods result in the formation of a composition comprising a target nucleic acid sequence and a nucleic acid probe capable of annealing to the target nucleic acid sequence to form a complex, wherein the nucleic acid probe comprises a chemical moiety, which if modified or removed permits the nucleic acid probe to form a hairpin structure and disassociate from the complex. The nucleic acid probe further optionally comprises a detectable label. Depending upon the detection system employed, the nucleic acid probe may further comprise a quencher capable of quenching a signal from detectable label.

The design and use of the turnover probes of the invention will now be discussed with reference to FIGS. 1-3.

FIG. 1 shows an exemplary assay using a turnover probe of the invention. In this system, energy released by hairpin formation is used to clear the target of the detector probe. The potential energy is released by hairpin formation following "shortening" of the probing segment as a result of backbone cleavage. More specifically, the turnover probe initially is mixed with a target sequence under conditions that permit the probe to anneal to the target sequence, if the target sequence is present in the sample. Assuming that a target nucleic acid is present in the sample, the turnover probe hybridizes to the target sequence. Thereafter, a chemical reagent when applied to the sample, cleaves the probe at the chemical moiety (denoted as "X" in FIG. 1). In FIG. 1, the exemplary chemical moiety (X) is a cleavable bond in the probe. Upon cleavage of the bond, the probe is broken into two pieces, at least one of which is capable for forming a hairpin structure. For example, in FIG. 1, cleavage of the bond yields a short fragment and a hairpin fragment. As a result of the formation of the hairpin structure, the probe becomes disassociated from the target leaving the target available for another hybridization event. The disassociation event is optionally coupled to a signal generation system so that a discrete signal is created (for example, an increase or decrease in fluorescence) when the probe turns over in the assay. The dissociation event optionally is coupled to the release of a bioactive compound such as a drug, vitamin, co-factor, toxin, immunogen, or the like.

Figure 2:
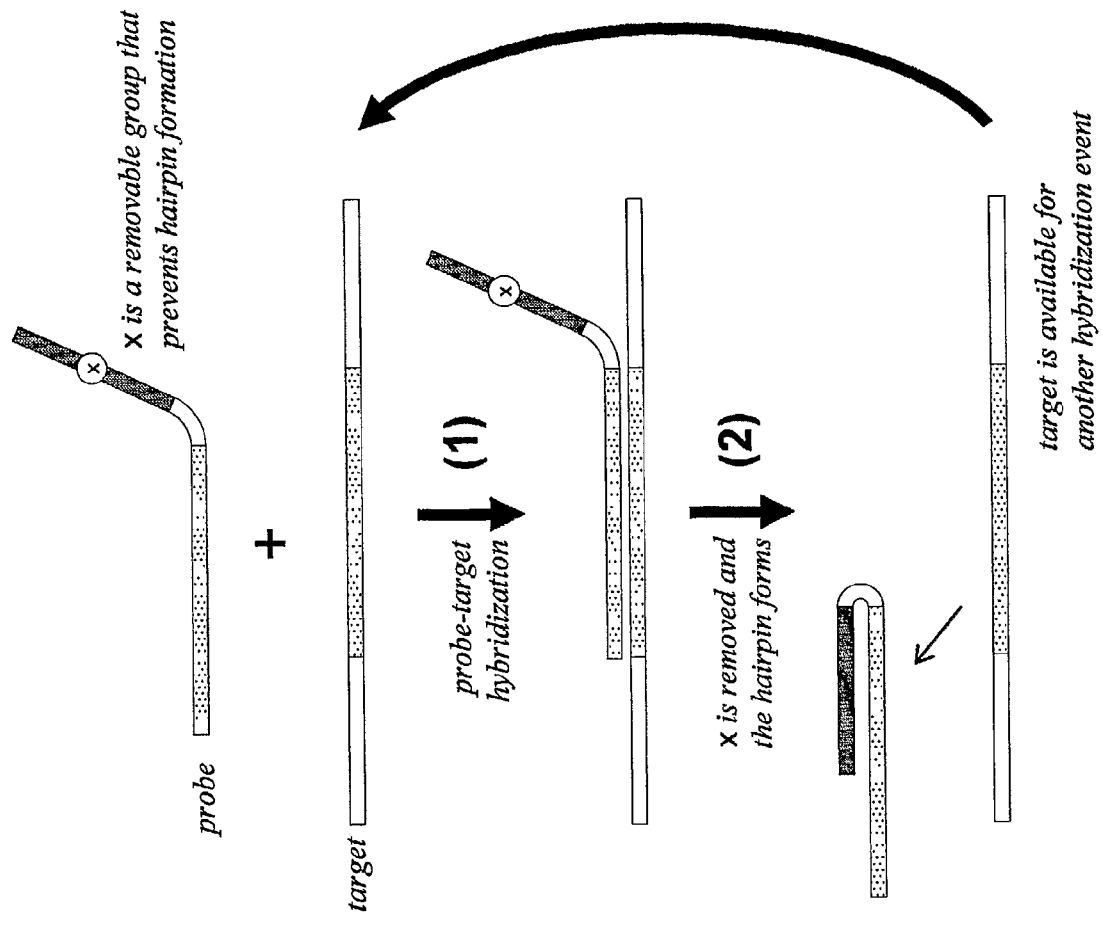
FIG. 2 is a schematic representation of a nucleic acid detection assay where the turnover probe is modified to produce a hairpin structure.

FIG. 2 shows another exemplary assay using a turnover probe of the invention. In this system, as well as the system shown in FIG. 1, energy released by hairpin formation is used to clear the target of the detector probe. The potential energy is released by hairpin formation as a result of unmasking a portion of the sequence in such a way that residues unable to participate in stem formation are now able to do so. More specifically, the turnover probe initially is mixed with a target sequence under conditions that permit the probe to anneal to the target sequence if the target sample is present in the sample. Assuming that a target nucleic acid is present in the sample, the turnover probe hybridizes to the target sequence. Thereafter, a chemical reagent when applied to the sample unmasks a masking group, denoted as "X" in FIG. 2. The masking group (X) is a removable group that prevents hairpin formation and can be, for example, a covalently linked short oligonucleotide cleavable from probe. The blocking oligonucleotide can be either attached through a cleavable internucleotide backbone or through some other type of linker. The masking group might also be a bulky, yet non-oligonucleotide substituent attached to one of the nucleobase heterocycles so as to disrupt the ability of the sequence to hybridize. Once the masking group (X) has been removed, the probe then is capable of forming a hairpin structure. As a result of the formation of the hairpin structure, the probe becomes disassociated from the target leaving the target available for another hybridization event. The disassociation event optionally is coupled to a signal generation system so that a discrete signal is created (for example, an increase or decrease in fluorescence) when the probe turns over in the assay. The dissociation event optionally is coupled to the release of a bioactive compound such as a drug, vitamin, co-factor, toxin, immunogen, or the like.

Figure 4:
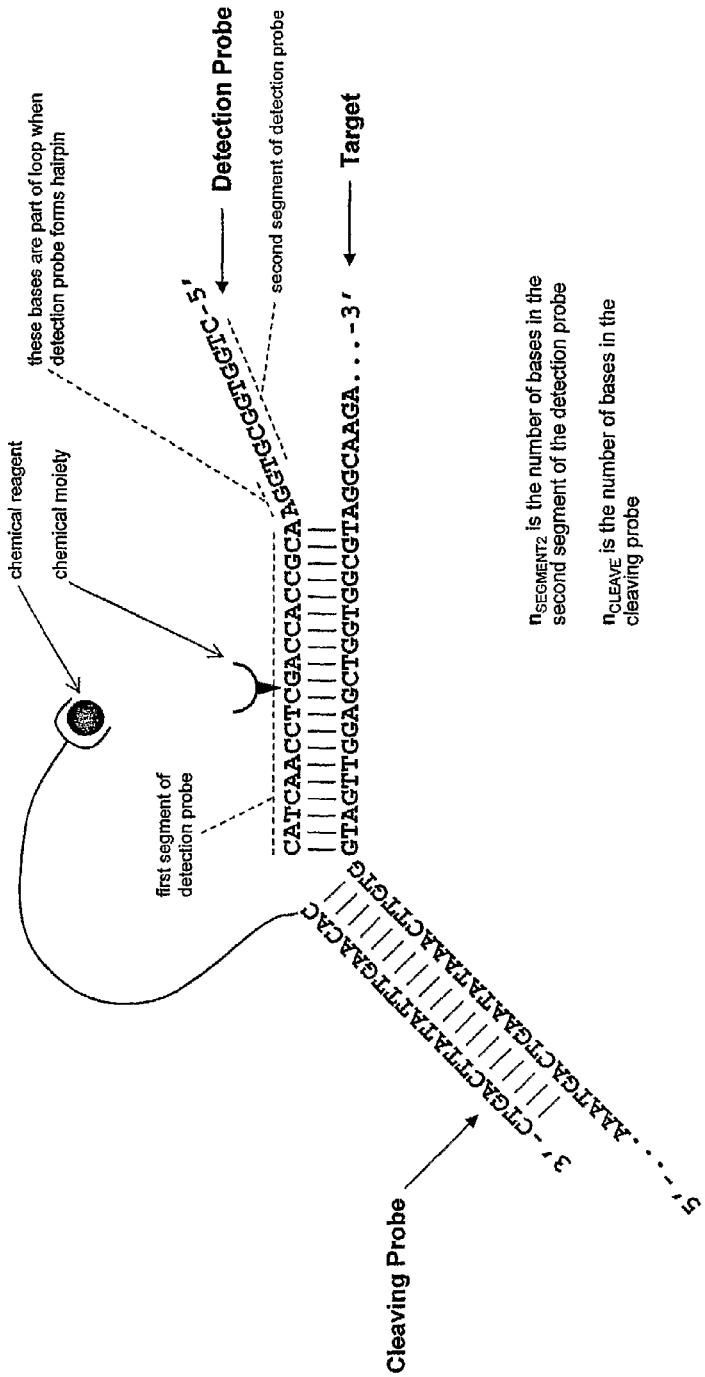
FIG. 4 is a schematic representation of an exemplary nucleic acid detection assay, where a Cleaving Probe, when annealed to a target nucleic acid, cleaves the Detection (turnover) Probe, when the Detection Probe is annealed to the target nucleic acid.
Figure 6:
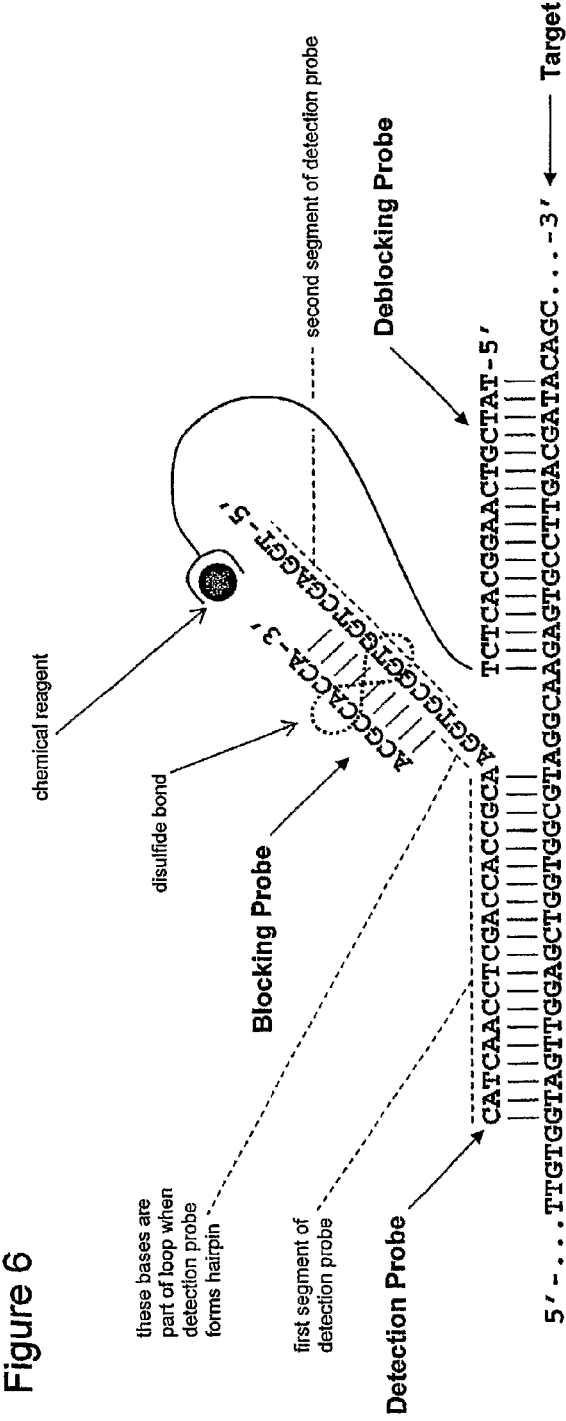
FIG. 6 is a schematic representation of an exemplary nucleic acid detection assay, where a Deblocking Probe, when annealed to a target nucleic acid, modifies (e.g., deblocks) a blocking probe disulfide bonded to a Detection (turnover) Probe, when the Detection Probe is annealed to the target nucleic acid.

It is contemplated that the chemical, enzymatic, or catalytic reactivity required to, for example, cleave the bond in FIG. 1, or to, for example, unmask the sequence in FIG. 2, can come from an additional reagent probe adjacent to the probe to be cleaved or unmasked (see, for example, FIGS. 4 and 6, respectively). Assays using such probes can be designed so that excess of the reagent probe is at or near unit equilibrium with target complex to ensure there is sufficient turnover of reagent on the target to facilitate a constant supply of active reagent probe on-target. Furthermore, the reagent probe provides additional specificity in the assay since it must hybridize to a sequence adjacent to the detector probe for the reaction to occur.

Figure 3:
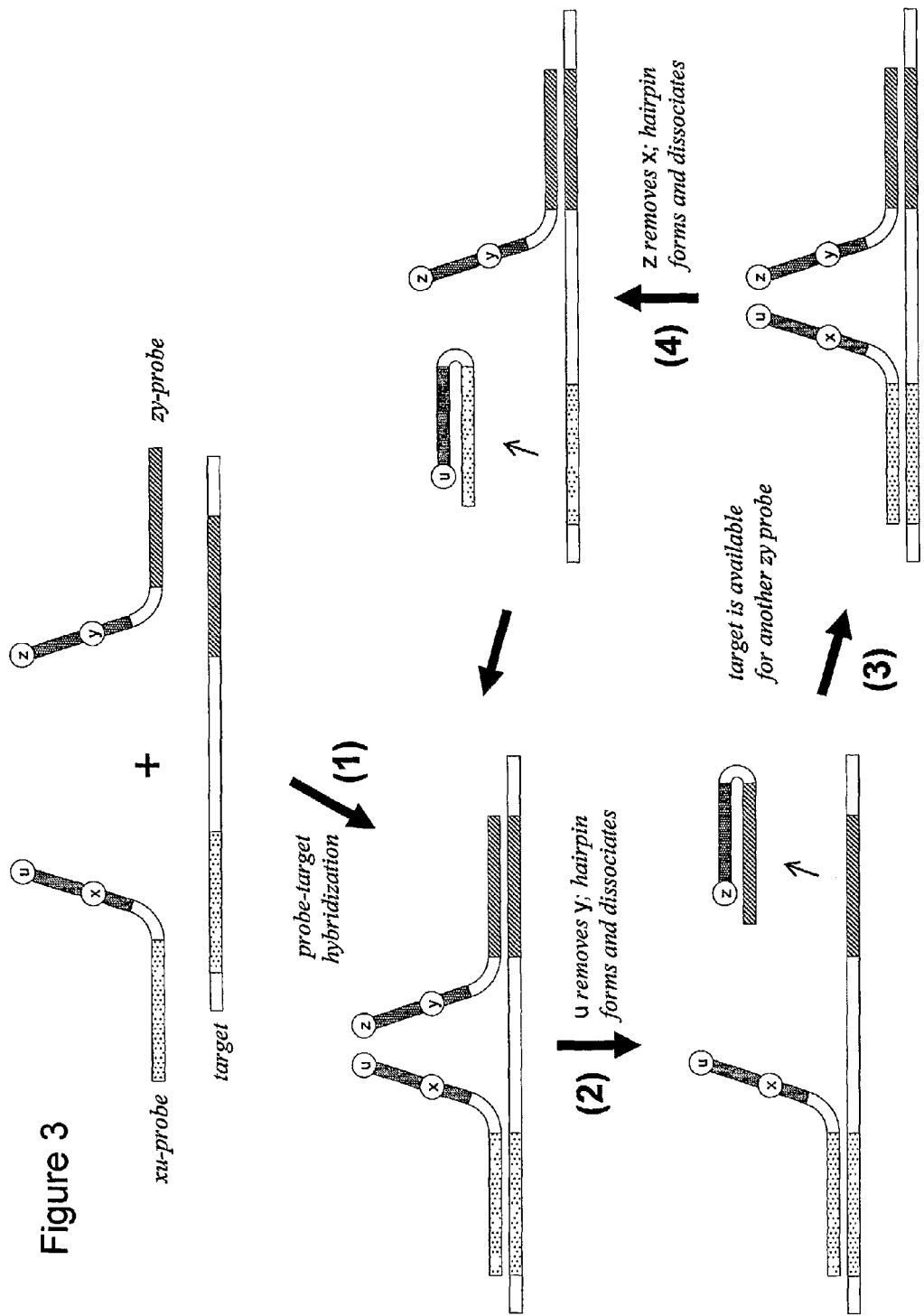
FIG. 3 is a schematic representation of a nucleic acid detection assay employing two different turnover probes, wherein a first probe (xu-probe) contains a reagent that modifies a second probe (zy-probe) so that the second probe forms a hairpin structure and disassociates from a duplex formed with the target nucleic acid, and a fresh, second probe, when it binds to the target nucleic acid contains a reagent that modifies the first probe so that the first probe disassociates from the duplex formed with the target nucleic acid.

FIG. 3 illustrates the unmasking of two turnover probes by one another where both probes have propensity to form hairpin structures, In this scheme, each masked probe also contains a reagent that will unmask the other probe. The reagent on either probe may be consumed in the unmasking process or it may be catalytic and not consumed. In FIG. 3, the reagent on the probe is consumed, so that once a probe unmasks an adjacent probe, the chemically spent probe must wait for hybridization of a fresh adjacent probe in order that it be unmasked and released from the target. A new molecule of the first probe then hybridizes and the cycle repeats itself. By extension of these principles it is possible to design a similar assay in which one member of a probe pair cleaves the other member of the probe pair.

More specifically, FIG. 3 shows a system comprising two hairpin probes. A first probe (denoted the xu-probe) comprises a removable blocking group (denoted as "X") that prevents hairpin formation and a functional group (denoted as "U") that unmasks a removable blocking group (denoted as "Y") in a second probe. The second probe (denoted the zy-probe) comprises removable blocking group Y and a functional group (denoted as "Z") that unmasks the removable blocking group X in the first probe. In the initial phase (denoted by "1") both probes anneal to the target sequence. In the next phase (denoted by "2"), functional group U of the first probe unmasks the removable blocking group Y of the second probe. As a result, the second probe then forms a hairpin structure and disassociates from the target permitting a fresh second probe to bind to the target sequence.

In the next phase (denoted by "3"), a second zy-probe anneals to the target. In the next phase (denoted by "4"), the functional group of the second probe Z then unmasks the removable blocking group X of the first probe. As a result, the first probe then forms a hairpin structure and disassociates from the target permitting a fresh first probe to bind to the target sequence. Hairpin formation of the first and second probes can be coupled to appropriate signal generation systems to amplify the resultant signal.

A key feature of the turnover probes of the invention is that when modified or cleaved, the probe forms a hairpin structure. Hairpin structures typically comprise first and second sequences complementary to, and capable of annealing to, one another. The first and second sequences create a stem structure when they anneal to one another. In the resulting hairpin structure, a first end of the first sequence is linked to a first end of the second sequence by a linker sequence of bases that do not anneal to one another.

In order to be able to create a hairpin structure once the chemical moiety has been cleaved or modified, the probes are designed to include three segments (see, FIG. 4). The first segment is defined by a first nucleic acid sequence that is complementary to a target nucleic acid sequence. The first segment comprises, for example, from 5 to 25, from 5 to 20, or from 10 to 25 residues in length. The second segment is defined by a second nucleic acid that is capable of annealing intramolecularly to the first nucleic acid sequence. The second segment comprises, for example, from 2 to 25, from 5 to 25, or from 2 to 20 residues in length. The third segment is defined by a linker sequence, for example, from 0 to 5 residues in length that does not anneal to either the first or second nucleic acid sequences. The first and second nucleic acids anneal to one another to produce the stem of the hairpin structure. The linker sequence produces the looped or head portion of the hairpin structure when the detection probe forms a hairpin.

The choice of the various probe segments will depend upon, for example, the target sequence to be analyzed, the concentration of the target and turnover probes, the assay conditions (for example, temperature, pH, salts, salt concentrations, buffers, and buffer concentrations, and other assay reagents such as alcohols and formamide), the complementarity or stability between the first and second segments of the probes, the size of the hairpin loop, and the sequence of the target. The design of various exemplary probes is discussed in more detail with reference to FIGS. 4-7.

FIG. 4 is a schematic representation of an exemplary nucleic acid assay wherein the chemical reagent (as part of the Cleaving Probe in FIG. 4) cleaves the chemical moiety in the turnover probe (denoted in FIG. 4 as the "Detection Probe"). In FIG. 4, the Detection Probe has the sequence 5'-CTGGTG-GCGTGGAACGCCACCAGCTCCAACTAC-3' (SEQ ID NO; 1). The number of bases in the second segment of the Detection Probe, $n_{SEGMENT2}$, is 10, and is represented as the first ten bases on the 5' end of the probe. The Cleaving Probe has the sequence 5'-CACAAGTTTATATTCAGTC-3' (SEQ ID NO: 2), and the number of bases in the Cleaving Probe, $n_{CLEAVE}$, is 19. The target has the sequence 5'-ATTATAAG-GCCTGCTGAAAATGACTGAATATAAACT-TGTGGTAGTTGGAGCTGGTGG CGTAGGCAAGAGT-GCCTTGACGA-3' (SEQ ID NO: 3). Both the Cleaving Probe and Detection Probe are shown annealed to the target sequence. A portion of the Detection Probe (first segment) is shown annealed to the target sequence and a portion of the Detection Probe (second segment) is not annealed to the target sequence. Upon cleavage of the chemical moiety in the Detection Probe, the second segment becomes capable of annealing to the first segment to form a hairpin structure. The third segment is part of the loop when the Detection Probe forms the hairpin structure.

Variations in the length of the second segment of the Detection Probe as a function of the bound probe were explored by performing simulations using the OMP (Oligonucleotide Modeling Program) available commercially (DNA Software, Ann Arbor Mich.), where pre-cleavage state (two probes and a target) and post-cleavage state (a probe, two probe fragments, and a target) were simulated separately from each other for each parameter value. The results are shown in FIGS. 5A-5E. FIG. 5A is a graph that shows the percentage of the Detection Probe bound to the target as a function of $n_{SEGMENT2}$, the number of bases in segment 2 of the Detection Probe prior to cleavage of the Detection Probe. The results indicate that, in general, as the $n_{SEGMENT2}$ increases in length, the amount of uncleaved probe bound to the target sequence decreases until $n_{SEGMENT2}$ is 10 to 11 residues when no more probe is bound. Conversely in this example, when $n_{SEGMENT2}$ is less than 10, almost all of the uncleaved probe is bound to the intended target sequence. The dotted-line curves in the graph in FIG. 5A represent simulation values when a mutant target was used. A point mutation at the end of the recognition site of the target sequence has an effect on the amount of the probe attached to the target site. Furthermore, a point mutation in the middle of the target has a more significant affect on the amount of probe bound to the target when $n_{SEGMENT2}$ is greater than 7 residues, The results show that for a range of $n_{SEGMENT2}$ values, the Detection Probe anneals to the target in a sequence specific manner and that mismatches adversely affect the binding of the Detection Probe allowing for specificity in the hybridization reaction.

FIG. 5B is a graph that shows the percentage of the "Short fragment" (see FIG. 1) of the Detection Probe that is bound to the target as a function of $n_{SEGMENT2}$ after cleavage of the Detection Probe. The graph indicates that, under the conditions examined, the short fragments of the probe only remain bound to the target when $n_{SEGMENT2}$ is less than 7 residues, and that when $n_{SEGMENT2}$ is greater than 7 residues both the shortened probe and hairpin forming probe are no longer annealed to target. This simulation indicates that upon Detection Probe cleavage, the two resulting pieces derived from the cleaved Detection Probe would dissociate from the target, thus providing the target available for hybridization of another full-length Detection Probe.

FIG. 5C is a graph that shows the percentage of the "Hairpin fragment" (see FIG. 1) of the Detection Probe that is bound to the target as a function of $n_{SEGMENT2}$ after cleavage of the detection probe. The graph indicates that, under the conditions examined, the hairpin fragments of the probe only remain bound to the target, when $n_{SEGMENT2}$ is less than 7 residues. In other words, under the conditions examined, the hairpin fragment of the probe is almost completely disassociated from the target when $n_{SEGMENT2}$ is greater than 7 residues.

FIG. 5D is a graph that shows the percentage of the "Cleaving Probe" bound to the target as a function of $n_{SEGMENT2}$ prior to cleavage of the Detection Probe. The graph indicates that, under the conditions examined, more than 50% of the Cleaving Probe is bound to the target for all $n_{SEGMENT2}$ lengths.

FIG. 5E is a graph that shows the percentage of the "Cleaving Probe" bound to the target as a function of $n_{SEGMENT2}$ after cleavage of the Detection Probe. The graph indicates that, under the conditions examined, more than 50% of the Cleaving Probe is bound to the target for all $n_{SEGMENT2}$ lengths.

Figure 5:
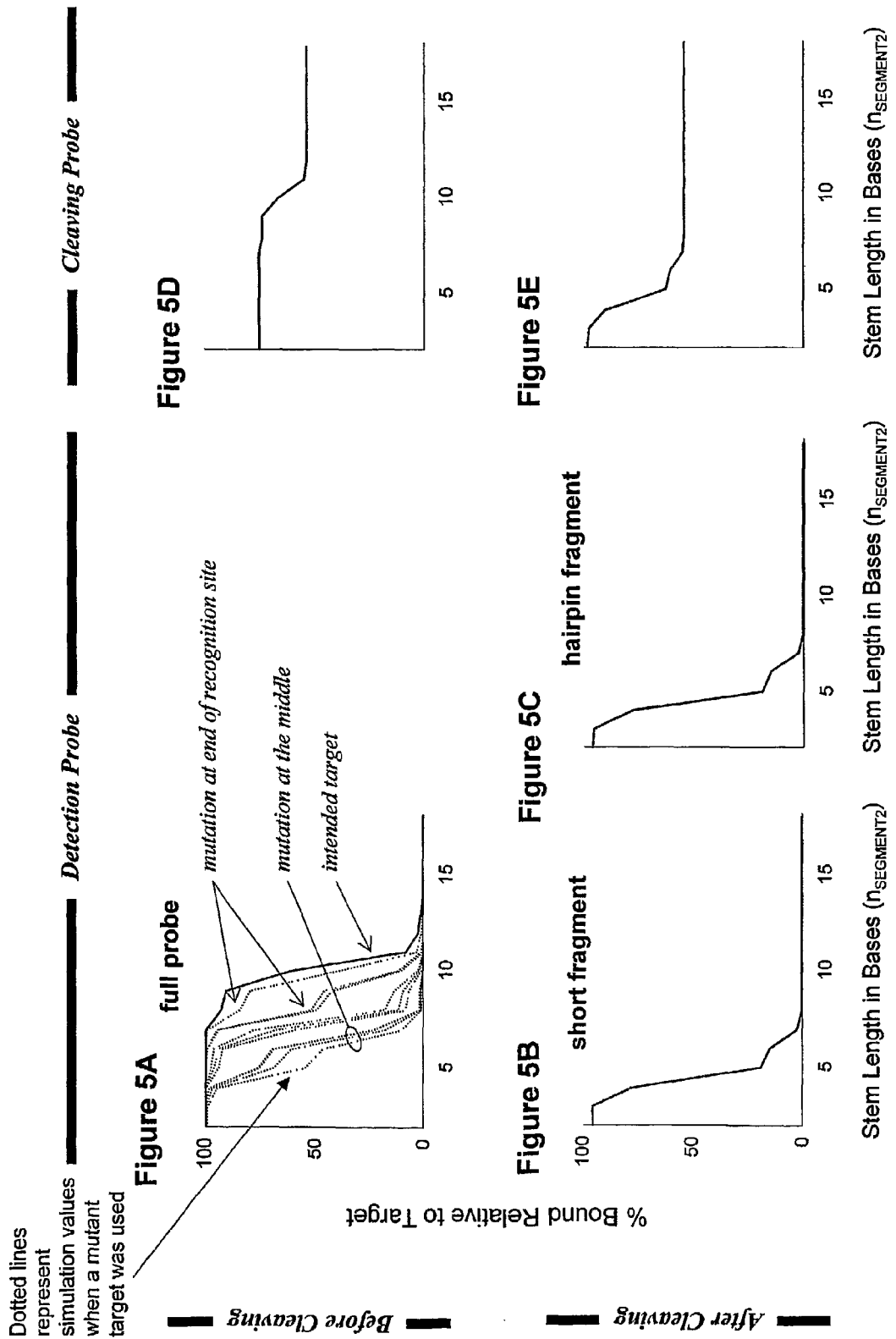
FIGS. 5A-5E are graphs that show the melting curves of the Detection and Cleaving Probes of FIG. 4 before and after cleavage, for example, an exemplary Detection Probe bound to the target before cleavage of the Detection Probe (FIG. 5A); the short fragment of the Detection Probe after cleavage of the Detection Probe (FIG. 5B); the hairpin fragment of the Detection Probe after cleavage of the Detection Probe (FIG. 5C); an exemplary Cleaving Probe bound to the target before cleavage of the Detection Probe (FIG. 5D); and the Cleaving Probe bound to the target after cleavage of the Detection Probe (FIG. 5E).

When taken together, FIGS. 4 and 5 A-E, indicate that a system containing (i) a Cleaving Probe, carrying a chemical reagent capable of promoting cleavage of an adjacent properly configured Detection Probe, and (ii) a Detection Probe with a properly configured cleavage site, can lead to probe turnover of the Detection Probe as a result of cleavage of a hairpin-forming Detection Probe.

FIG. 6 is a schematic representation of another exemplary nucleic acid assay where a Blocking Probe, when attached to a turnover probe (denoted in FIG. 6 as a "Detection Probe") prevents the Detection Probe from forming a hairpin structure. In this figure, the Blocking Probe is covalently linked to the Detection Probe by means of a disulfide bond as represented by the dashed line in FIG. 6. The Blocking Probe has the sequence 5'-ACGCCACCA-3' (SEQ ID NO: 4) and the number of bases in the Blocking Probe, $n_{BLOCK}$, is 9. The Detection Probe has the sequence 5'-TGGAGCTGGTG-GCGTGGAACGCCACCAGCTCCAACTAC-3' (SEQ ID NO: 5) and the number of bases in the second section of the Detection Probe, $n_{SEGMENT2}$, is 15, and is represented as the first fifteen bases on the 5' end of the probe. The target has the sequence 5'-TGACTGAATATAAACTTGTGGTAGTTG-GAGCTGGTGGCGTAGGCAAGAGTGCCTTG ACGATACAGCTAATTCAGAATCAT-3'(SEQ ID NO: 6). The Deblocking Probe has the sequence 5'-TATCGTCAAG-GCACTCT-3' (SEQ ID NO: 7), and the number of bases in the Deblocking Probe, $n_{DEBLOCK}$, is 17.

In this assay, the chemical reagent (as part of the "Deblocking Probe" in FIG. 6) reduces the disulfide bond so that the Blocking Probe can become disassociated from the Detection Probe. Both the Deblocking Probe and Detection Probe are shown annealed to the target sequence. A portion of the Detection Probe (first segment) is shown annealed to the target sequence and a portion of the Detection Probe (second segment) is not annealed to the target sequence. Upon reduction of the disulfide bond, the Blocking Group becomes disassociated from the second segment of the Detection Probe. As a result, the second segment of the Detection Probe becomes capable of annealing to the first segment of the Detection Probe to form a hairpin structure. The third segment of the Detection Probe becomes part of the loop when the Detection Probe forms the hairpin structure. This type of assay is described in Example 3.

Figure 7:
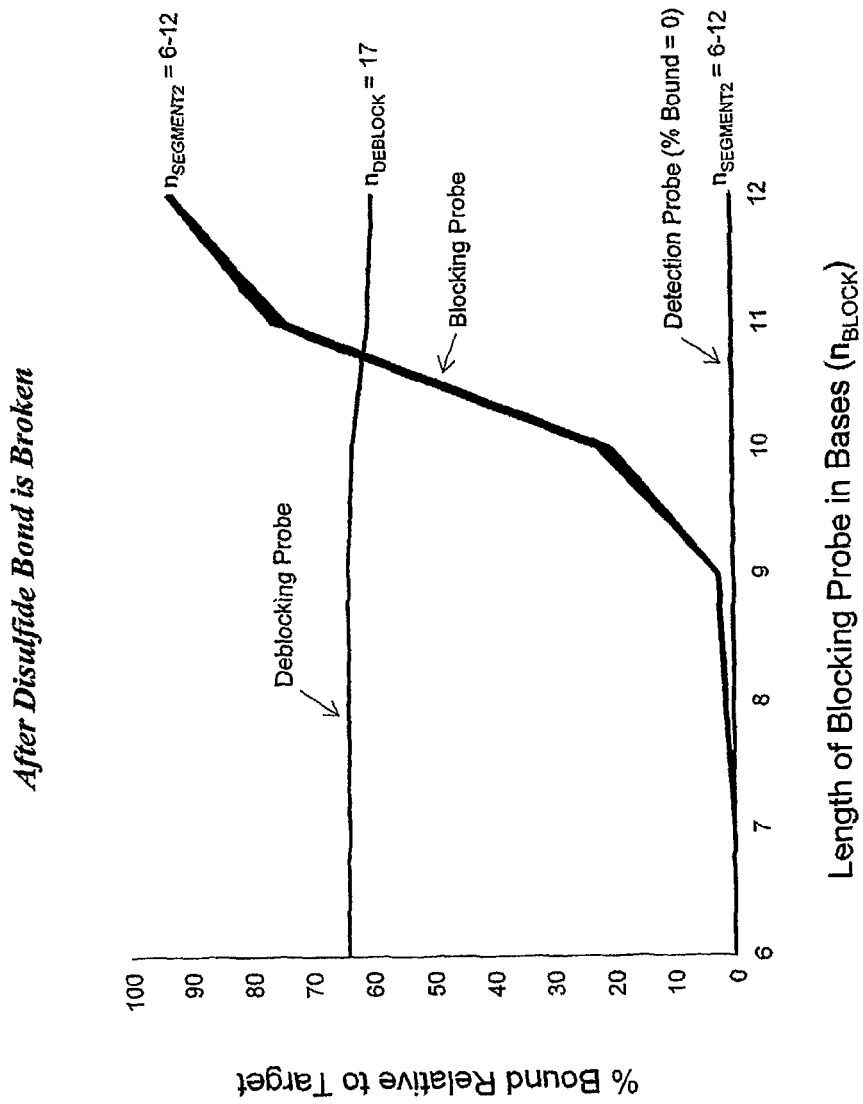
FIG. 7 is a graph showing the melting curves of the Deblocking Probe, the Blocking Probe and the Detection Probe of FIG. 6, once the disulfide bond that links the Blocking and Detection Probes has been broken.

FIG. 7 shows the percentage of the Blocking Probe, Deblocking Probe, and Detection Probe Bound to the target as the length of the Blocking Probe following breakage of the disulfide bond. Under the conditions examined, the percentage of bound Deblocking Probe ($n_{DEBLOCK}=17$) bound to target is ~60-70% regardless of the lengths of $n_{SEGMENT2}$ and $n_{BLOCK}$ indicates that it will hybridize to the target and will be available to break the disulfide bond between the Detection Probe and the Blocking Probe. Moreover after the disulfide bond is broken, the released Detection Probe ($n_{SEGMENT2}=6-12$) does not anneal to the target for any value of $n_{BLOCK}$ and $n_{SEGMENT2}$. If the Blocking Probe is sufficiently short (e.g., less than 10 residues), it also will not anneal to target, therefore making the target available hybridization of new Detection Probe ($n_{SEGMENT2}=6-12$). The percentage of bound blocking probe is not affected by $n_{SEGMENT2}$ for the values shown.

It is understood that the turnover probes may be constructed from DNA, RNA, LNA, PNA and their analogues and mixtures thereof. It is understood that the term "nucleic acid" embraces DNA, RNA, LNA, PNA and their analogues and mixtures thereof. Linkers may be constructed from nucleotides or from a linear non-nucleotide polymer such as PEG, PPG, aliphatic chains, a polypeptide, polyalkylphosphates etc., in which case the polymer connecting the first and second sequences will be from 2 to 50 atoms in length. It should be noted that the first and second nucleic acid sequences may be located at the 5' and 3' ends of the probe, respectively, or they may be reversed.

The probes further contain a chemical moiety associated with the nucleic acid sequence, which if modified or removed by a chemical reagent permits the probe to form a hairpin structure and to disassociate from the complex. Useful chemical moieties can be selected from the group consisting of a chemical bond, (for example, an internucleotide linkage), an atom, a base, a modified base, an oligonucleotide, a modified oligonucleotide, a bulky substituent such as a peptide, branched polypeptide, cyclic polypeptide, or other bulky substituents such as porphyrins, dendrimers, etc. Under certain circumstances, the chemical moiety is disposed within the nucleic acid sequence. Under other circumstances, the chemical moiety is attached, for example, via a covalent linkage, to the nucleic acid sequence.

There are a number of chemical moieties and/or masking groups that can be used to cleave, block or unmask the probes in these systems. For example, various sulfur containing internucleotide linkages can be reduced or cleaved by metals to break the probe backbone (see, for example, Kuimelis & McLaughlin Nucl. Acids Res. (1995) 23, 4753, Mag et al., Nucl. Acids Res. (1991) 19, 1437, Metelev, et al., Nucl. Acids Res. (2001) 29, 4062). The metals or reducing agents can be delivered to the sulfur bond within a cleavable probe by an adjacent probe having a chelation or reducing group attached. Oligonucleotides with pendant chelators and reducing compounds have been described in U.S. Pat. Nos. 6,831,166 and 5,980,861.

There are numerous other chemical possibilities for probe backbone cleavage. For example, a phosphines can be employed to reduce an azide (such as those azides shown below) to create an amine. The amine then attacks the adjacent carbonyl group forming an amide or urea heterocycle with resultant backbone cleavage. Alternatively, properly protected amine functions could also be deprotected to generate the nucleophile that would attack and cleave the backbone.

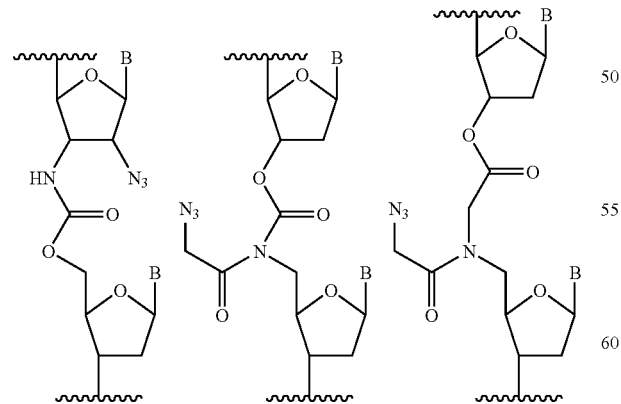

Masked thiol linkages can also be employed for backbone cleavage as these are known to facilitate strand scission when deprotected. See for example, Fidanza and McLaughlin, J. Amer. Chem. Soc. (1992) 57, 2340. One of many possible configurations of masked thiol is shown below and such linkages can be readily prepared. When the thiol masking group is a disulfide, the thiol can be unmasked using a reducing agent such as a phosphine. The unmasked thiol then reacts intramolecularly to cleave the strand as shown below.

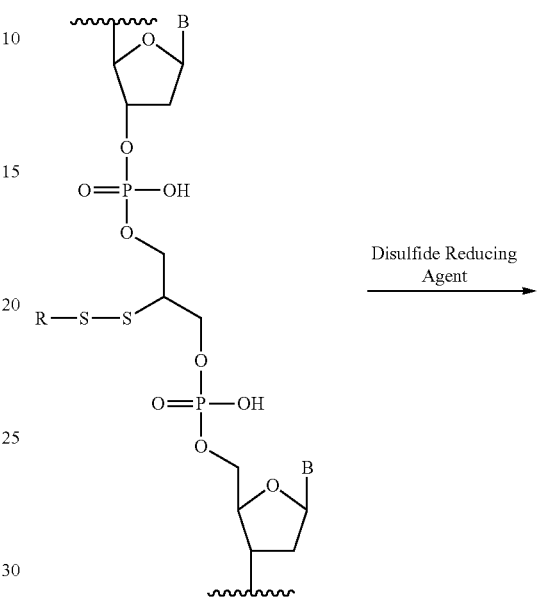

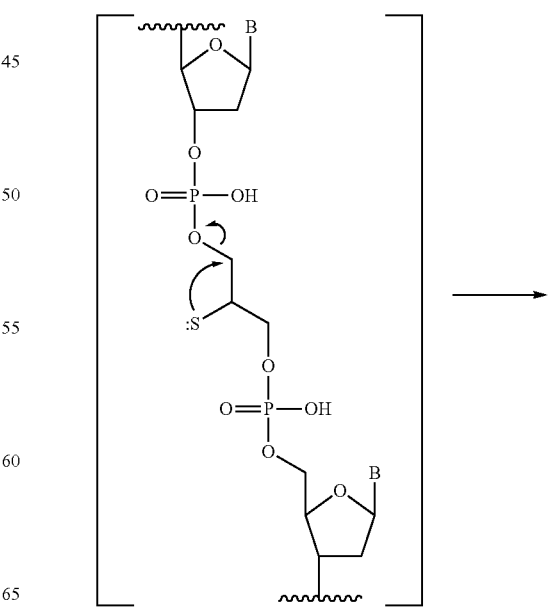

-continued

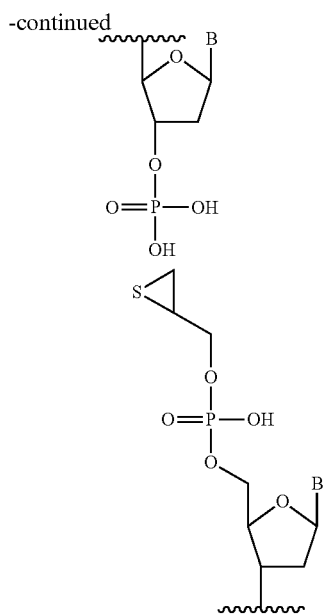

Probes are conjugated to various signal generation systems. The signal, when generated, is detected by a detection system that reports the progress of the turnover reaction. For example, dyes and quenchers may be placed within the probes such that fluorescence resonance energy transfer (FRET) is created or destroyed as the probes are cut and/or unmasked. Examples of specific fluorophores and FRET technologies useful in the practice of the invention include are described in U.S. Pat. Nos. 6,485,901 and 6,103,476. Masking groups can be chemical moieties that become fluorescent or colored upon removal of the masking group from the probe. Masking groups can also be enzyme co-factors such NADH, pyridoxal, flavin mononucleotide (FMN) and the like, which upon release complement an enzyme to make it active. That enzyme may then operate on a substrate that produces color, light, fluorescence or some other measurable signal, or the enzyme might be part of an enzyme cascade that produces a measurable signal. Examples of enzyme systems useful in the practice of the invention, include diaphorease, alcohol dehydrogenase, FMN oxidoreductase, among others. The masking group can also be a peptide or protein that when released becomes active or complements another peptide, protein, or molecule to generate a measurable activity. For example, the masking group could be S-peptide which is able to complement S-protein to generate S-RNAse (Richards and Logue, J. Biol. Chem. (1962) V 249, pp 2285-2293). There are many other possible reporter systems that can be linked to probes and assays of this invention.

There are significant advantages to the described systems. These include the ability of the target (template) to cause turnover of the probes in a way that is expected to be faster (takes advantage of hairpin potential energy) and more specific (utilizes two adjacent probes as well as required chemistry) than either Cycling Probe Technology or the probe turnover systems known in the art. It is contemplated that with the appropriate probe design it is possible to achieve turnovers significantly greater than 1,000 cycles in a 30 minute period.

Because the probes are completely synthetic they are inexpensive to manufacture, can be made at large scale, and are easily redesigned if needed. The system is also flexible in that it may be used for detection of non-nucleic acid targets, for example by coupling the template to an antibody or other binding molecule (e.g., small molecule, co-factor, glycan, peptide, etc.), with all the added benefits that the turnover aspect imparts.

Practice of the invention will be more fully understood from the following non limiting examples, which are presented herein for illustrative purpose only, and should not be construed as limiting in anyway.

EXAMPLE 1

The following Example describes an embodiment of the present invention in which a first oligonucleotide probe can be cleaved by a second oligonucleotide probe to detect the presence of a third oligonucleotide.

A first oligonucleotide (Oligo1) having the sequence: 3'-CATCAACCTCxGACCACCGCAAGGTGCG-GTGGTC-5' (SEQ ID NO: 1) where (x) denotes a bridging phosphorothioate linkage is prepared according to the method of Mag et al., Nucleic Acids Research (1991) V. 19, pp 1437-1441.

A second oligonucleotide (Oligo2) having the sequence: 3'-CTGACTTATATTTGAACACy-5' (SEQ ID NO: 2) where (y) denotes an amine connected to the oligonucleotide by a 56 atom spacer is prepared by synthesis of a 5'-amine derivatized oligonucleotide according to Morocho et al., Bioconjugate Chem (2004) V. 15, pp 569-575. The cleaved, purified, amine-derivatized oligonucleotide is reacted with the NHS or p-nitrophenyl ester of p-chloromecurybenzoic acid according to Schmidt et al., Biochemical and Biophysical Research Communications (1972) Vol 48 (2) pp 461-456 and Levy, Biochimica et Biophysica Acta (1973) Vol 317 (2) pp 473-481 to provide after HPLC purification the oligonucleotide with a pendant phenyl mercury group (Oligo2Hg).

A third oligonucleotide (Oligo3) having the sequence: 5'-ATTATAAGGCCTGCTGAAAATGACT-GAATATAAACTTGTGGTAGTTGGAGCTGGTGG CGTAGGCAAGAGTGCCTTGACGATACAGC-3' (SEQ ID NO: 3) is purchased from Integrated DNA Technologies (Coralville, Iowa USA).

Oligo3 is combined with Oligo2Hg and Oligo1 in a buffer containing aqueous sodium chloride and sodium phosphate, optionally, magnesium chloride, and, optionally formamide. In order to determine the buffer and reaction conditions that promote the cleavage of Oligo1 by Oligo2 while they are hybridized to Oligo 3, separate reactions are performed in which the concentration of each oligonucleotide is varied between 1 and 1,000 nM, the sodium chloride concentration is varied from 0.05 to 1 M, the phosphate concentration is fixed at 0.05 M and the pH is varied between 4 and 10, magnesium chloride concentration is varied between 0 and 10 mM, and the amount of formamide as a percent of the total volume is varied between 0 and 70 percent. The temperature of some of the reactions is also varied from 10 to 70° C.

The reaction progress can be monitored by gel electrophoresis for the presence of the Oligo1 cleavage products. Control reactions omitting various components, most notably Oligo3, are used to determine that the cleavage is due to hybridization of Oligo1 and Oligo2 to Oligo3. The amount of cleavage products can be quantitated by gel electrophoresis or by HPLC.

EXAMPLE 2

The following Example describes an embodiment of the present invention in which a first oligonucleotide probe can be cleaved by a second oligonucleotide probe to detect the presence of a third oligonucleotide.

Oligo1 and Oligo3 are prepared as described in Example 1. Oligo2 bearing an amino group is prepared as described in Example 1, then the amine is derivatized with a chelator using the reagent Isothiocyanato-EDTA available from Dojindo Molecular Technologies (Gaithersburg Md., USA) according to the manufacturer's instructions. Aliquots of the purified oligonucleotide (Oligo2Ch), bearing the chelator, are incubated with various divalent metal cation chloride salts, notably $MgCl_2$, $CaCl_2$, $MnCl_2$, $CoCl_2$, $ZnCl_2$, $CdCl_2$, and $HgCl_2$, in Tris-HCl at pH 7.0 to effect coordination of the metal by the pendant chelate group. Excess metal is removed by dialysis or desalting the oligonucleotide by binding, washing then elution from a C18 reversed-phase cartridge.

The divalent cation-loaded oligonucleotides are then combined with Oligo1 and Oligo3 under various condition as described in Example 1 to determine reaction conditions that promote cleavage of Oligo1 by metal-loaded Oligo2Ch.

EXAMPLE 3

The following Example describes an embodiment of the present invention in which a cross linked pair of oligonucleotides can be cleaved by another oligonucleotide to detect the presence of an oligonucleotide target.

An oligonucleotide (Oligo4) having the sequence: 5'-ACGCCA*CCA-3' (SEQ ID NO: 4) where (*) represents a thiol modification to the adenine residue is prepared according to Ferentz et al. (1991) J. Amer. Chem. Soc., V 113, pp 4000-4002.

Another oligonucleotide (Oligo5) having the sequence: 3'-CATCAACCTCGACCACCGCAAGGTGCGGT*GGT CGAGGT-5'(SEQ ID NO: 5) where (*) represents a thiol modification to the 5-position of the thymine residue is prepared by first synthesizing a 5-carboxyl modified DNA utilizing Carboxy dT (Glen Research, Sterling Va., USA) according to the manufacturer's instructions and then converting this to the thiol by first forming an amide by reacting the carboxyl group with aminoethanethiol disulfide according to the Glen Research User Guide of DNA Modifications (1999, pp 37). The disulfide is cleaved and the oligonucleotide purified according to Bischoff et al. (1987) Analytical Biochemistry 164, 336-344.

Oligo4 and Oligo5 are hybridized and cross linked through formation of a disulfide bond according to Ferentz et al. The cross-linked product (Oligo6) is purified by gel electrophoresis and reversed-phase HPLC.

An oligonucleotide (Oligo7) having the sequence: 3'-TCTCACGGAACTGCTAT-5' (SEQ ID NO: 7) bearing a 3'-terminal phosphine is prepared according to Sakurai et al. (2005) J. Amer. Chem. Soc., V 127, pp 1600-1661.

Oligo6 is combined with Oligo7 and Oligo3 in a buffer containing aqueous sodium chloride and sodium phosphate, optionally magnesium chloride, and optionally formamide. In order to ascertain the buffer and reaction conditions that promote the disassociation of Oligo6 by Oligo7 while they are hybridized to Oligo3, separate reactions are performed in which the concentration of each oligonucleotide is varied between 1 and 1,000 nM, the sodium chloride is varied from 0.05 to 1 M, the phosphate concentration is fixed at 0.05 M and the pH is varied between 4 and 10, magnesium chloride concentration is varied between 0 and 10 mM, and the amount of formamide as a percent of the total volume is varied between 0 and 70 percent. The temperature of some of the reactions is also varied from 10 to 70° C.

The reaction progress is monitored by gel electrophoresis for the formation of Oligo4 and Oligo5 and for the disappearance of Oligo6. Control reactions omitting various components, most notably Oligo3, are used to determine that the cleavage is due to hybridization of Oligo6 and Oligo7 to Oligo3. The amount of cleavage products are quantitated by gel electrophoresis or optionally by HPLC.

EXAMPLE 4

The following Example describes an embodiment of the present invention in which a first oligonucleotide probe can be cleaved by a second oligonucleotide probe to detect the presence of a third oligonucleotide.

Figure 8:
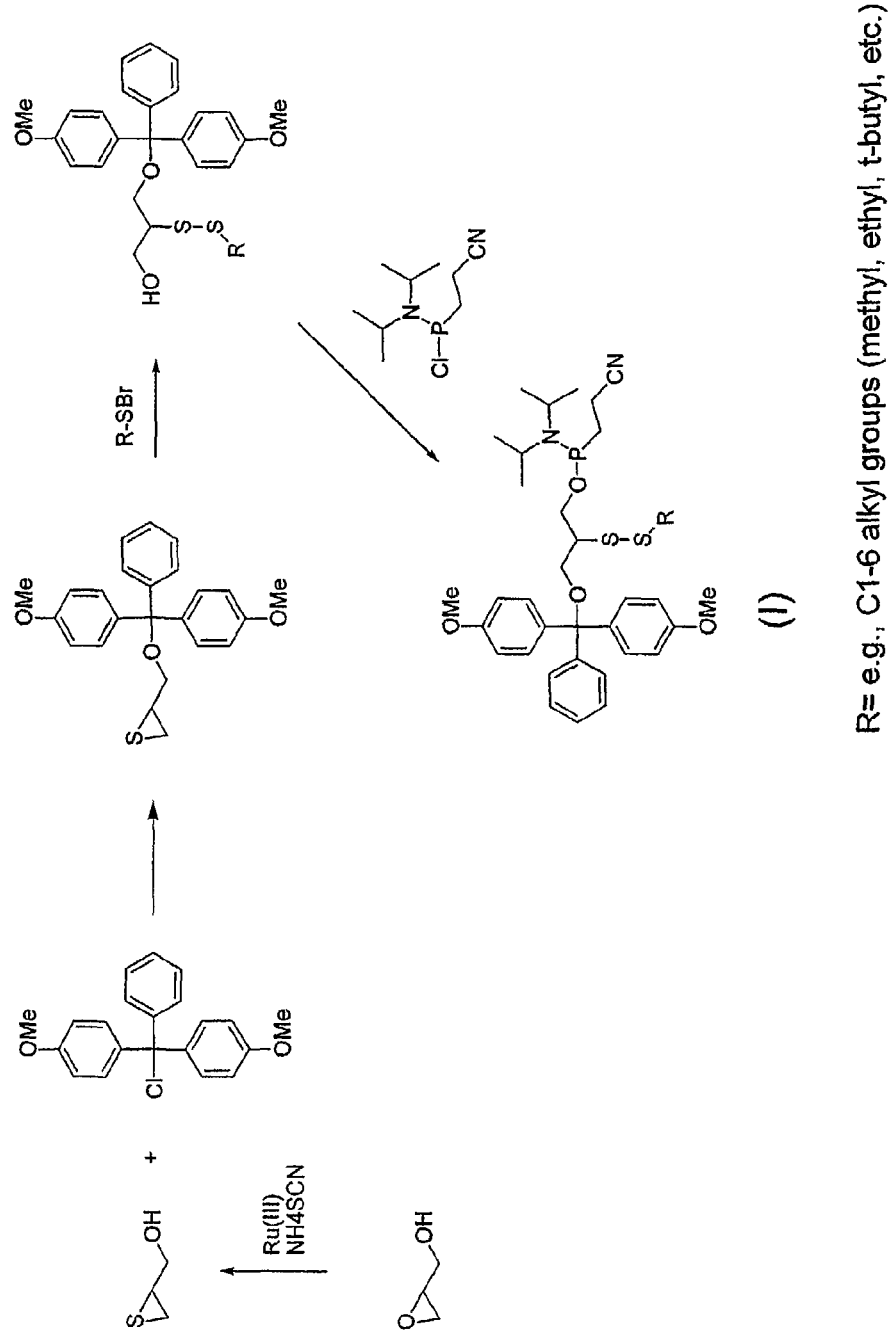
FIG. 8 is an exemplary chemistry scheme illustrating the synthesis of a phosphoramidite monomer that can be used to incorporate a cleavable linker into an oligonucleotide.

A phosphoramidite containing a masked thiol is prepared according to the synthetic scheme depicted in FIG. 8. Glycidol is converted to 3-hydroxy-1,2-propylene thiirane according to Iranpoor and Kazemi, Tetrahedron (1997) V. 53, pp 11377-11382. The hydroxyl group then is protected as the dimethoxytrityl ether (DMT). Thiirane ring opening is accomplished by treatment with an alkenylsulfenyl bromide, followed by bromide displacement with silver acetate, and the acetate group was removed using methanolic sodium methoxide. These last three steps are accomplished as described by Silvestri and Wong, J. Org. Chem. (2001) V. 66, pp 910-914. The resulting alcohol then is converted to the beta-cyanoethyl phosphoramidite as described by Sinha et al., Nuc. Acids. Res., (1984) V 12, pp 4539.

With the phosphoramidite described in the previous paragraph, an eighth oligonucleotide (Oligo8) having the sequence: 3'-CCATCAACCTxGACCACCGCAAGGT-GCGGTGGTC-5' (SEQ ID NO: 8) where (x) denotes a masked disulfide containing linkage is prepared according to standard methods for synthesis of oliognucleotides using phosphormadite chemistry (see Chapter 1, in Oligonucleotides and Analogues; A Practical Approach, Eckstein, F. ed., IRL Press, (1991))

A ninth oligonucleotide (Oligo9) having the sequence:3'-ACTGACTTATATTTGAACAy-5' (SEQ ID NO: 9) where (y) denotes a triphenylphosphine moiety connected to the oligonucleotide by a 56 atom spacer is prepared by synthesis of a 5'-amine derivatized oligonucleotide according to Morocho et al., Bioconjugate Chem (2004) V. 15, pp 569-575. The 5'-amine protecting group is removed and the resin bound, amine-derivatized oligonucleotide is reacted with p-carboxyphenyl-diphenylphosphine by adapting the method of Sakurai et al. (2005) J. Amer. Chem. Soc., V 127, pp 1600-1661 for the preparation of 3'-triphenylphosphine labeled oligonucleotides. Oligo9 is then cleaved from the support, deprotected and purified according to Sakurai.

Oligo3 as prepared in Example 1 is combined with Oligo8 and Oligo9 in a buffer containing aqueous sodium chloride and sodium phosphate, optionally, magnesium chloride, and, optionally formamide. In order to determine the buffer and reaction conditions that promote the cleavage of Oligo8 by Oligo9 while they are hybridized to Oligo 3, separate reactions are performed in which the concentration of each oligonucleotide is varied between 1 and 1,000 nM, the sodium chloride concentration is varied from 0.05 to 1 M, the phosphate concentration is fixed at 0.05 M and the pH is varied between 4 and 10, magnesium chloride concentration is varied between 0 and 10 mM, and the amount of formamide as a percent of the total volume is varied between 0 and 70 percent. The temperature of some of the reactions also is varied from 10 to 70° C.

The reaction progress can be monitored by gel electrophoresis for the presence of the Oligo1 cleavage products. Control reactions omitting various components, most notably Oligo3, are used to determine that the cleavage is due to hybridization of Oligo8 and Oligo9 to Oligo3. The amount of cleavage products can be quantitated by gel electrophoresis or by HPLC.

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing form the spirit or essential characteristics thereof. The foregoing embodiments are therefore to be considered in all respects illustrative rather than limiting on the invention described herein, Scope of the invention is thus indicated by the appended claims rather than by the foregoing description, and all changes that come within the meaning and range of equivalency of the claims are intended to be embraced therein.

What is claimed is:

1. A composition comprising a nucleic acid probe capable of annealing to a target nucleic acid to form a complex, wherein the probe comprises
   (i) a nucleic acid sequence complementary to the target nucleic acid;
   (ii) a chemical moiety associated with the nucleic acid sequence, which if modified or removed by a chemical reagent permits the probe to form a hairpin structure and to disassociate from the complex, wherein the chemical moiety is selected from the group consisting of a base, a modified base, an oligonucleotide, a modified oligonucleotide, a modified internucleotide linkage, a protecting group, a peptide, a protein, a polymer, a bead and a nanoparticle;
   (iii) a signal generating moiety associated with the nucleic acid sequence; and
   (iv) optionally, a signal quencher associated with the nucleic acid sequence.

2. A method of amplifying a signal indicative of the presence of a target nucleic acid in a sample, the method comprising the steps of:
   (a) incubating a sample suspected of containing the target nucleic acid with a first nucleic acid probe under conditions to permit the first nucleic acid probe to anneal to the target nucleic acid if present in the sample, wherein the first nucleic acid probe comprises (i) a signal generating moiety capable of producing a detectable event and (ii) a nucleotide sequence that anneals to the target nucleic acid;
   (b) providing a non-enzymatic turnover inducing reagent that reacts with the first nucleic acid probe to promote separation of the first nucleic acid probe from the target nucleic acid and create a detectable event; and
   (c) allowing a second nucleic acid probe to bind to the target nucleic acid after the first nucleic acid probe has been separated from the target nucleic acid and produce another detectable event.

3. The method of claim 2, wherein the signal generating moiety is covalently attached to the target nucleic acid.

4. The method of claim 2, wherein the signal generating moiety is a catalyst.

5. The method of claim 2, wherein the signal generating moiety is a light emitting moiety.

6. The method of claim 2, wherein the detectable event is an optical event.

7. The method of claim 6, wherein the optical event comprises a fluorescent event.

8. The method of claim 2, wherein the turnover inducing reagent is attached to a different nucleotide sequence that anneals to the target nucleic acid at a location adjacent to where the probe anneals to the target nucleic acid.

9. The method of claim 2, wherein the turnover inducing reagent reacts with the first nucleic acid probe to cause the first nucleic acid probe or a fragment thereof produce a hairpin structure.

10. The method of claim 9, wherein the detectable event occurs after hairpin formation.

11. A method of disassociating a nucleic acid probe from a target nucleic acid sequence, the method comprising the steps of:
   (a) combining a nucleic acid probe with a sample suspected of containing the target nucleic acid sequence under conditions to permit the probe to anneal to the target nucleic acid sequence to form a complex if the target nucleic acid is present in the sample, wherein the nucleic acid probe comprises a chemical moiety, which if modified or removed, permits the nucleic acid probe or a fragment thereof to form a hairpin structure and disassociate from the complex, wherein the chemical moiety comprises a thiol linkage masked by a disulfide moiety produced using the phosphoramidite as shown in FIG. 8 (compound I) wherein R is a linear or branched $C_{1-6}$ alkyl group; and
   (b) providing a reagent capable of modifying or removing the chemical moiety so that if the complex is present in the sample the nucleic acid probe or the fragment thereof forms a hairpin structure and disassociates from the complex.

12. A composition comprising a nucleic acid probe capable of annealing to a target nucleic acid to form a complex, wherein the probe comprises
   (i) a nucleic acid sequence complementary to the target nucleic acid;
   (ii) a chemical moiety associated with the nucleic acid sequence, which if modified or removed by a chemical reagent permits the probe to form a hairpin structure and to disassociate from the complex, wherein the chemical moiety comprises a thiol linkage masked by a disulfide moiety produced using the phosphoramidite as shown in FIG. 8 (compound I) wherein R is a linear or branched $C_{1-6}$ alkyl group:,
   (iii) a signal generating moiety associated with the nucleic acid sequence; and
   (iv) optionally, a signal quencher associated with the nucleic acid sequence.

13. A composition comprising a target nucleic acid sequence and a nucleic acid probe capable of annealing to the target nucleic acid sequence to form a complex, wherein the nucleic acid probe comprises a chemical moiety, which if modified or removed permits the nucleic acid probe to form a hairpin structure and disassociate from the complex, wherein the chemical moiety comprises a thiol masked by a disulfide linkage produced using the phosphoramidite as shown in FIG. 8 (compound I) wherein R is a linear or branched $C_{1-6}$ alkyl group.

14. The method of claim 2, wherein the chemical moiety comprises a masked thiol linkage produced using the phosphoramidite as shown in FIG. 8 (compound I) wherein R is a linear or branched $C_{1-6}$ alkyl group.

* * * * *

```
                             SEQUENCE LISTING

<160> NUMBER OF SEQ ID NOS: 9

<210> SEQ ID NO 1
<211> LENGTH: 33
<212> TYPE: DNA
<213> ORGANISM: Artificial
<220> FEATURE:
<223> OTHER INFORMATION: Exemplary Detection Probe

<400> SEQUENCE: 1
ctggtggcgt ggaacgccac cagctccaac tac                              33

<210> SEQ ID NO 2
<211> LENGTH: 19
<212> TYPE: DNA
<213> ORGANISM: Artificial
<220> FEATURE:
<223> OTHER INFORMATION: Exemplary Cleaving Probe

<400> SEQUENCE: 2
cacaagttta tattcagtc                                              19

<210> SEQ ID NO 3
<211> LENGTH: 80
<212> TYPE: DNA
<213> ORGANISM: Artificial
<220> FEATURE:
<223> OTHER INFORMATION: Exemplary Target Sequence

<400> SEQUENCE: 3
attataaggc ctgctgaaaa tgactgaata taaacttgtg gtagttggag ctggtggcgt    60
aggcaagagt gccttgacga                                               80

<210> SEQ ID NO 4
<211> LENGTH: 9
<212> TYPE: DNA
<213> ORGANISM: Artificial
<220> FEATURE:
<223> OTHER INFORMATION: Exemplary Blocking Probe

<400> SEQUENCE: 4 acgccacca                                                           9

<210> SEQ ID NO 5
<211> LENGTH: 38
<212> TYPE: DNA
<213> ORGANISM: Artificial
<220> FEATURE:
<223> OTHER INFORMATION: Exemplary Detection Probe

<400> SEQUENCE: 5
tggagctggt ggcgtggaac gccaccagct ccaactac                           38
```

-continued

```
<210> SEQ ID NO 6
<211> LENGTH: 80
<212> TYPE: DNA
<213> ORGANISM: Artificial
<220> FEATURE:
<223> OTHER INFORMATION: Exemplary Target

<400> SEQUENCE: 6
tgactgaata taaacttgtg gtagttggag ctggtggcgt aggcaagagt gccttgacga      60
tacagctaat tcagaatcat                                                  80

<210> SEQ ID NO 7
<211> LENGTH: 17
<212> TYPE: DNA
<213> ORGANISM: Artificial
<220> FEATURE:
<223> OTHER INFORMATION: Exemplary Deblocking Probe

<400> SEQUENCE: 7
tatcgtcaag gcactct                                                     17

<210> SEQ ID NO 8
<211> LENGTH: 33
<212> TYPE: DNA
<213> ORGANISM: Artificial
<220> FEATURE:
<223> OTHER INFORMATION: Oligo8

<400> SEQUENCE: 8
ctggtggcgt ggaacgccac cagtccaact acc                                   33

<210> SEQ ID NO 9
<211> LENGTH: 19
<212> TYPE: DNA
<213> ORGANISM: Artificial
<220> FEATURE:
<223> OTHER INFORMATION: Oligo9

<400> SEQUENCE: 9
acaagtttat attcagtca                                                   19
```